United States Patent [19]
Houben et al.

[11] Patent Number: 6,135,978
[45] Date of Patent: Oct. 24, 2000

[54] SYSTEM FOR PANCREATIC STIMULATION AND GLUCOSE MEASUREMENT

[75] Inventors: Richard P. M. Houben, Berg & Terblijt; Alexis C. M. Renirie, Berg en Dal; Koen J. Weijand, Hoensbroek, all of Netherlands

[73] Assignee: Medtronic, Inc., Minneapolis, Minn.

[21] Appl. No.: 09/273,463

[22] Filed: Mar. 22, 1999

Related U.S. Application Data

[62] Division of application No. 08/876,738, Jun. 16, 1997.

[51] Int. Cl.$^7$ .................................................. A61M 31/00
[52] U.S. Cl. ............................... 604/66; 600/365; 607/72
[58] Field of Search .................................... 600/345, 347, 600/365; 604/65–67; 607/72

[56] References Cited

U.S. PATENT DOCUMENTS

| | | | |
|---|---|---|---|
| 4,003,379 | 1/1977 | Ellinwood, Jr. | 128/260 |
| 4,403,984 | 9/1983 | Ash et al. | 604/50 |
| 4,431,004 | 2/1984 | Bessman et al. | 128/635 |
| 4,704,029 | 11/1987 | Van Heuvelen | 356/39 |
| 5,101,814 | 4/1992 | Palti | 128/638 |
| 5,113,859 | 5/1992 | Funke | 128/419 |
| 5,165,407 | 11/1992 | Wilson et al. | 128/635 |
| 5,190,041 | 3/1993 | Palti | 128/635 |
| 5,231,988 | 8/1993 | Wernicke et al. | 128/421 |
| 5,362,307 | 11/1994 | Guy et al. | 604/20 |
| 5,919,216 | 7/1999 | Houben et al. | 607/72 |

OTHER PUBLICATIONS

"Kinetics of Intraperitoneally Infused Insulin in Rats—Functional Implications for the Bioartificial Pancreas"—Paul De Vos et al. (Diabetes, vol. 45, Aug. 1996).

Pancreatic Beta Cells are Bursting, but how?—Daniel L. Cook, et al. (TINS, vol. 14, No. 9, 1991).

*Primary Examiner*—Corrine McDermott
*Attorney, Agent, or Firm*—Thomas F. Woods; Michael J. Jaro; Harold Patton

[57] ABSTRACT

There is provided an implantable system and method for monitoring pancreatic beta cell electrical activity in a patient in order to obtain a measure of a patient's insulin demand and blood glucose level. A stimulus generator is controlled to deliver stimulus pulses so as to synchronize pancreatic beta cell depolarization, thereby producing an enhanced electrical signal which is sensed and processed. In a specific embodiment, the signal is processed to determine the start and end of beta cell depolarization, from which the depolarization duration is obtained. In order to reduce cardiac interference, each stimulus pulse is timed to be offset from the QRS signal which can interfere with the pancreas sensing. Additionally, the beta cell signals are processed by a correction circuit, e.g., an adaptive filter, to remove QRS artifacts, as well as artifacts from other sources, such as respiration. The thus obtained insulin demand signal is used either to control delivery of insulin from an implanted insulin pump, or to control ongoing pancreatic stimulation of a form to enhance insulin production.

2 Claims, 5 Drawing Sheets

SYSTEM FOR PANCREATIC STIMULATION AND GLUCOSE MEASUREMENT

This application is a divisional of Ser. No. 08/876,738 filed Jun. 16, 1997, pending.

FIELD OF THE INVENTION

This invention relates to systems for treatment of non-insulin-dependent diabetes mellitus and, in particular, systems for stimulating the pancreas to enhance sensing of beta-cell electrical activity, from which a measure of patient blood glucose level is obtained.

BACKGROUND OF THE INVENTION

It is known, from statistics published in 1995, that the number of diabetes patients in the United States is 7.8 million, or about 3.4% of the total U.S. population. This number has been steadily rising over the last 25 years. Approximately 90%, or about 7 million, are non-insulin-dependent diabetes mellitus (NIDDM) patients, in whom the sensitivity to rising glucose levels, or the responsiveness of insulin, is compromised to varying degrees. About 30%, or 2.3 million these patients, use insulin, and about 25% of these insulin users take daily measures of blood glucose levels. As a general proposition, most NIDDM patients are candidates for blood glucose level measurements and/or injections of supplemental insulin. The percentage of NIDDM patients receiving insulin treatment increases with the duration of NIDDM, from an initial rate of about 25% to about 60% after 20 years. For this population of patients, there is a need for a flexible and reliable system and method for measuring glucose level and supplying insulin when and as needed.

The human pancreas normally provides insulin for metabolic control. Basically, the insulin acts to promote transport of glucose in body cells. The pancreas has an endocrine portion which, among other functions, continuously monitors absolute blood glucose values and responds by production of insulin as necessary. The insulin-producing cells are beta cells, which are organized with other endocrine cells in islets of Langerhans; roughly 60-80% of the cells in an islet are such beta cells. The islets of Langerhans in turn are distributed in the pancreatic tissue, with islets varying in size from only about 40 cells to about 5,000 cells.

It has been observed that neighbor beta cells within an islet are coupled by gap junctions, which allow for electrical coupling and communication between neighboring beta cells. The beta cells within the islet undergo periodic depolarization, which is manifested in oscillatory electrical spikes produced by the beta cells, often referred to as burst which carries on for a number of seconds. The beta cell electrical activity is characterized by a low frequency alternation consisting of a depolarized phase (the burst) followed by a repolarized or hyperpolarized phase which is electrically silent. The relative time spent in the depolarized phase, during which the relatively higher frequency beta cell action potentials are triggered, has a sigmoidal relation with blood glucose concentration. The duty cycle, or depolarization portion compared to the quiet portion, is indicative of glucose level, and thus of insulin demand. Additionally, the frequency of the spikes during the active period, and likewise the naturally occurring frequency of the bursts (also referred to plateaus) carries information reflective of glucose level.

In view of the above, it is to be seen that sensing of the beta cell activity from islets of Langerhans in the pancreas may provide information for sensing insulin demand and controlling insulin delivery. Systems which seek to utilize glucose-sensitive living cells, such as beta cells, to monitor blood glucose levels, are known in the art. U.S. Pat. No. 5,190,041 discloses capsules containing glucose-sensitive cells such as pancreatic beta cells, and electrodes for detecting electrical activity. The capsules are situated similarly to endogenous insulin-secreting glucose-sensitive cells, and signals therefrom are detected and interpreted to give a reading representative of blood glucose levels. However, in this and other similar systems, the problem is in reliably sensing the beta cell electrical activity. It is difficult to determine the onset of the burst phase, and accurate determination of the spike frequency is difficult. This sensing problem is aggravated by cardiac electrical interference, as sensing of the QRS can mask portions of the islet electrical activity, particularly the onset of the burst depolarization phase. Thus, there is a need for a system which effectively and reliably utilizes the body's own glucose-monitoring system for obtaining accurate information concerning blood glucose level and insulin demand. Additionally, it is very desirable to provide for an effective response to rising insulin demand by activating an insulin pump, or by enhancing pancreatic insulin production.

SUMMARY OF THE INVENTION

It is an object of this invention to provide a system for improved sensing of pancreatic beta cell electrical activity, so as to determine insulin demand, i.e., blood glucose level. The system includes a stimulus generator for stimulating the pancreatic beta cells with electric field stimuli so as to provide synchronized burst responses which are relatively free of signal interference and which can be accurately timed. It is a further object of this invention to provide systems for sensing insulin demand and for responding by delivering insulin from a pump, or by stimulating the pancreas to cause increased insulin production by the pancreas (as disclosed in concurrently filed application Ser. No. 08/876,610 case P-7328, incorporated herein by reference).

In view of the above objects, there is provided a system and method for improved insulin delivery for an NIDDM patient. The system is based on sensing in-vivo pancreatic beta cell electrical activity, as an indictor for insulin demand. In a first embodiment, a pancreatic stimulus generator is controlled to deliver synchronized stimulus pulses, i.e., electric field stimuli, to the patient's pancreas at a slow rate, e.g., once every 6-20 seconds. Following a generated electric field stimulus, the depolarization activity of the cells is sensed and processed to derive an indication of blood glucose level. The system monitors cardiac activity, and controls the delivery of stimulus pulses so that the onset of each beta cell burst is relatively free of interference of the heart's QRS complex. The blood level information obtained from the sensed beta cell activity can be used for automatic control of an insulin pump. In another embodiment, the electric field stimuli are delivered to transplanted pancreatic beta cells in order to enhance insulin production, as disclosed in referenced Ser. No. 08/876,610. In yet another embodiment, the vagal nerve is stimulated to synchronize.

The blood glucose level monitoring may be carried out substantially continuously by an implantable system, or the system may be programmed for periodic measurement and response. In another embodiment, measurements may initiated by application of an external programmer, e.g., a simple hand-held magnet. In yet another embodiment of the invention, blood glucose level may also be monitored by another sensor, such as by examining EKG signals or nerve signals, and the system responds to insulin demand by controlling delivery of insulin from an implantable pump or by stimulating the pancreatic beta cells to enhance insulin production directly by the pancreas, also as disclosed in referenced Ser. No. 08/876,610.

DESCRIPTION OF THE PREFERRED EMBODIMENTS

Figure 1:
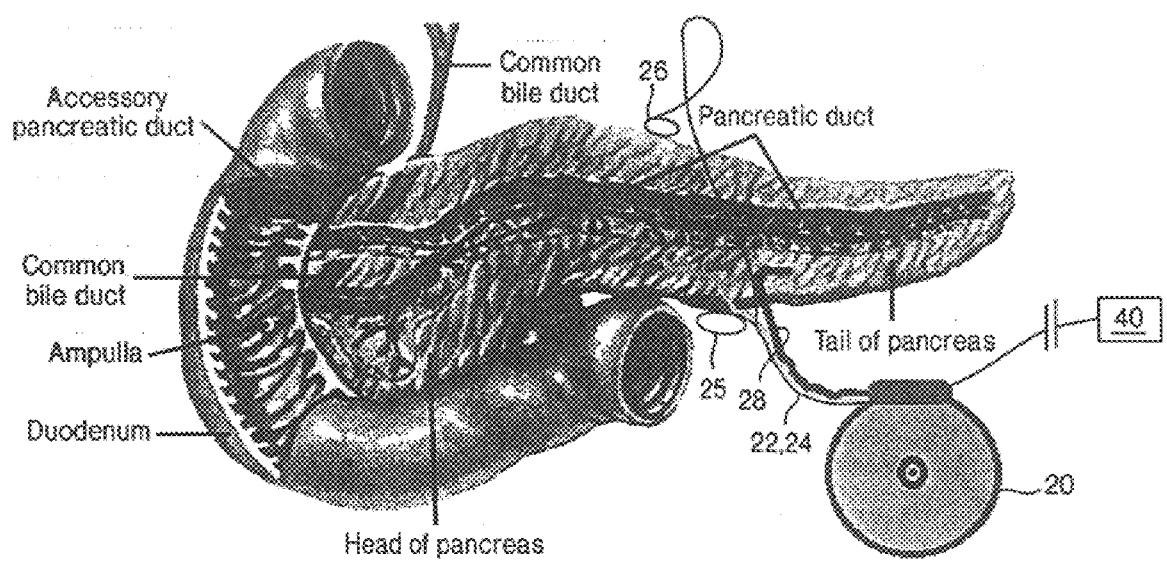
FIG. 1 is a diagram of a human pancreas with electrodes positioned for use in the system of this invention.

Referring now to FIG. 1, there is shown a diagram of a human pancreas, with an indication of some of the primary features of the pancreas. An implantable device 20 is illustrated, which suitably contains a stimulus generator and associated electronics, and an insulin pump. Of course, separate devices can be used, as a matter of design choice. A sensing lead 22 is illustrated which connects device 20 to one or more pairs of electrodes illustrated schematically at 25, 26, for use in stimulating and sensing. Although not specifically shown, a lead can be positioned into the pancreatic vein, carrying two or more large electrodes. Alternately, the system can employ one transvenous electrode and one epi-pancreatic electrode. Further, as discussed below, the stimulation and sensing can be done with a transplant of beta cell islets. An insulin delivery tube 28 is shown for delivery of insulin into the pancreas, preferably into the portal vein.

Figure 2A:
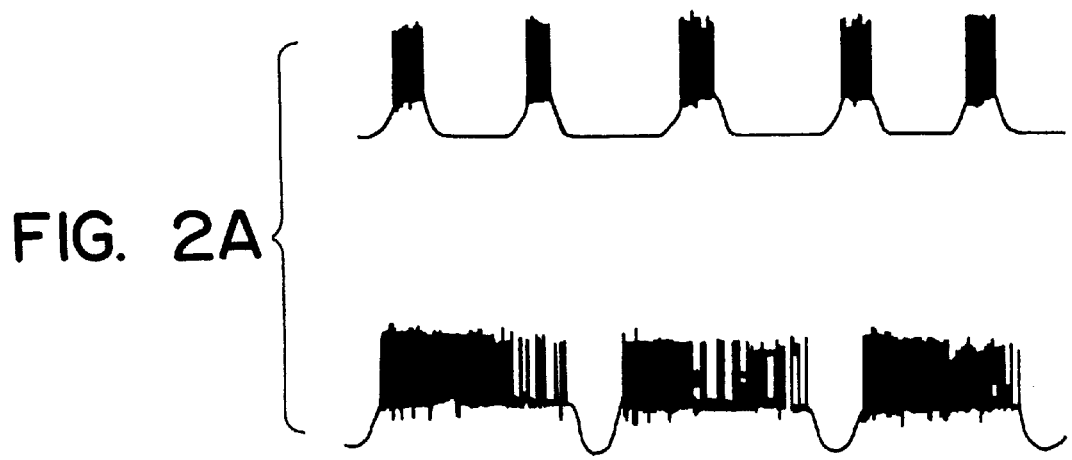
FIG. 2A shows two timing diagrams of beta cell electrical activity of islets of Langerhans, the upper diagram having a lower burst duty cycle, while the lower diagram has a higher burst duty cycle.
Figure 2B:
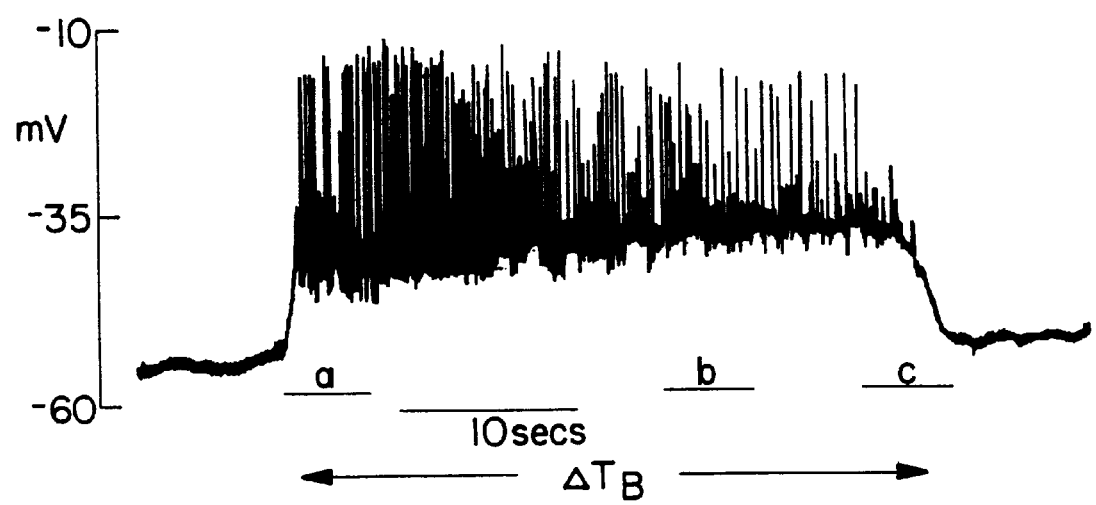
FIG. 2B is a timing diagram showing in greater detail the features of a depolarization burst portion of a cycle as depicted in either diagram of FIG. 2A.

Referring to FIG. 2A there are shown two timing diagrams illustrating the burst behavior of the beta cells of the pancreas, as described above. In the upper diagram, the duty cycle, defined as the fraction of the burst duration compared to the overall depolarization-repolarization cycle, is rather small. This represents a condition where glucose levels are low to moderate, and there is relatively little demand for insulin. The lower timing diagram indicates a situation of greater insulin demand characterized by a much higher duty cycle, with corresponding greater burst activity and concurrent insulin production. In an extreme situation, the burst activity would be virtually continuous. Referring to FIG. 2B, there is shown a blown up depiction of the burst or depolarization portion of the beta cell cycle. It is seen that the onset of depolarization is rather sharp, followed by relatively high frequency spiking. Toward the end of the burst period, the spike frequency is seen to diminish, and then the electrical activity simply tails off. However, the end of the burst period, as shown in this representation, is sharp enough to be able to define with substantial accuracy an end of burst time. As discussed above, the mean spike frequency carries information reflective of glucose level, but the duration of the burst, indicated as $T_B$, is the primary indication insulin demand, and thus of blood glucose level. As discussed in greater detail below, either $T_B$, or $T_B$ as a fraction of the low frequency depolarization-polarization cycle, may be used to determine blood glucose level.

Figure 3:
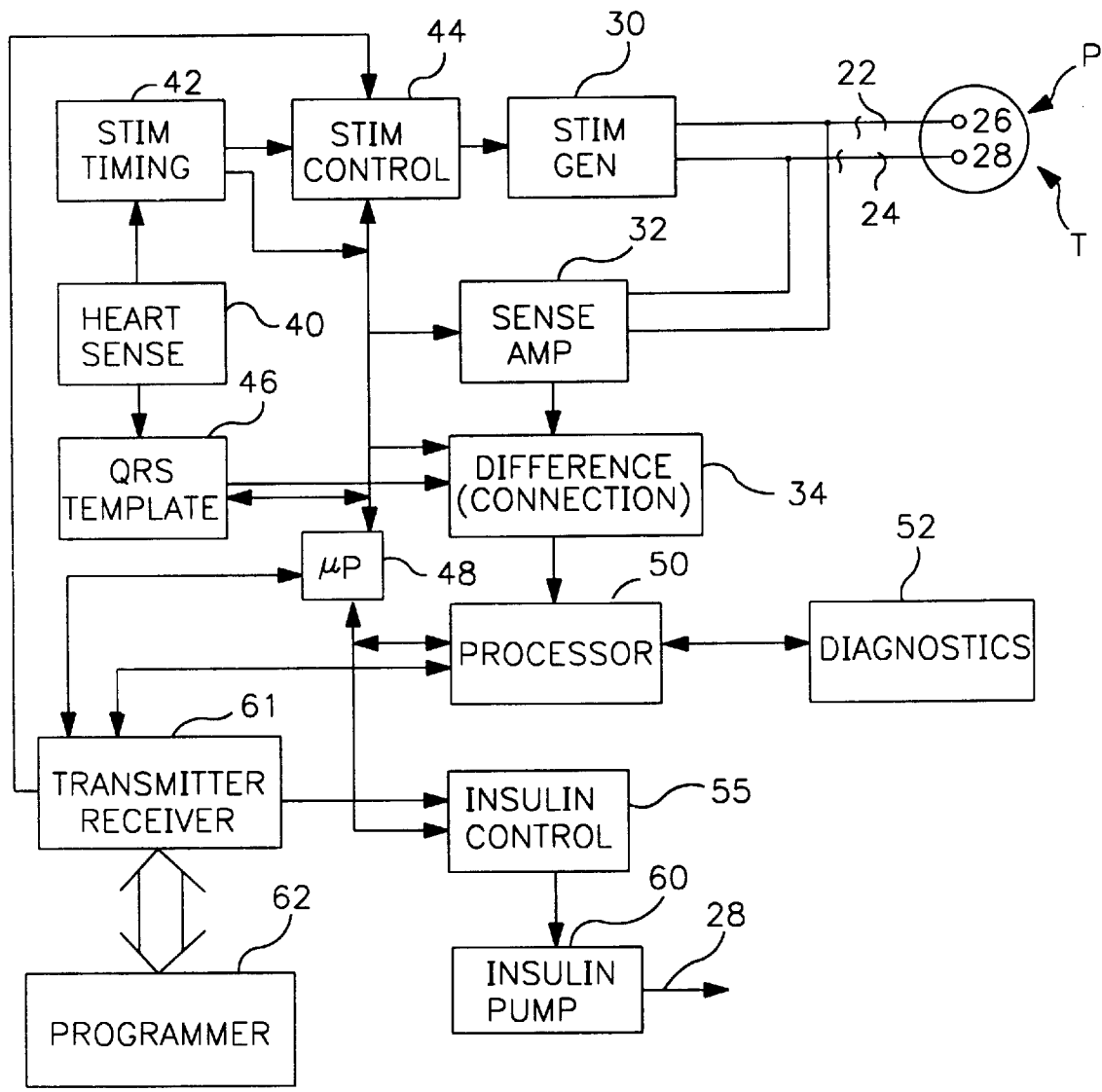
FIG. 3 is a block diagram showing the primary functional components of a system in accordance with this invention.

Referring now to FIG. 3, there is shown a block diagram of the primary components of a preferred embodiment of an implantable system in accordance with this invention. All of the components, except the heart sensor 40, may be housed in implantable device 20. A stimulus generator 30 produces stimulus pulses, under control of the stimulus control block 44, for delivering electric field stimuli. As used herein, the terms stimulus and pulse refer to generation of an electric field at a beta cell or nerve site. The pulses are delivered on lead conductors 22, 24, to the pancreas, designated by P; or to a transplant, shown as T. The signals sensed at electrodes 26, 28, i.e., the beta cell electrical activity signals, are communicated to sense amplifier 32. Amplifier 32 has suitable timing control and filters for isolating, as well as possible, the beta cell electrical activity from other interference signals. The sense signals are processed further with correction circuit 34, such as an adaptive filter, which subtracts out a QRS template as generated by block 46 whenever a QRS is detected. Although not shown in FIG. 3, correction circuit 34 may also suitably correct for artifacts originating from some other source, i.e., heart, respiration, stomach, duodemun and uterus. This is done to cancel out the interference effect of a QRS complex whenever it occurs during sensing of the beta cell burst. The output of correction circuit 34 is further processed at 50, where the time duration of the burst, $T_B$ is determined. Block 50 may also derive a measure of the mean spike frequency of the burst duration. This information transferred to memory associated with microprocessor 48, and also is stored at diagnostics block 52. Microprocessor 52 evaluates the stored data, and generates a control signal representative of insulin demand, or blood glucose level. Since insulin secretion, and thus insulin demand is derived from glucose driven intracellular processes, the terms insulin demand and glucose level are used interchangeably. The insulin demand signal which is connected to insulin control block 55, which produces a control signal for energizing insulin pump 60, which in turn ejects insulin through delivery tube 28.

A heart sensor 40 is suitably positioned in the vicinity of the pancreas, as also shown schematically in FIG. 1. The cardiac sensor output is connected to stimulus timing circuit 42, which times the QRS signals, and delivers a timing control signal to control block 44, the timing control signal being suitably delayed following the occurrence of a QRS. By this means, the stimulus generator is controlled to produce a pulse which is displaced from the QRS, thereby enabling clear detection of the onset of the beta cell burst. Thus, when microprocessor 48 delivers an enable signal to control 44 and there has been a predetermined delay following a QRS, a stimulus pulse is delivered. The heart sensor output is also connected to QRS template circuit 46, which generates a template signal which simulates the interfering QRS signal which would be sensed by the pancreatic electrodes 26, 28. The QRS template signal is inputted to correction circuit 34 coincident with sensing of a QRS complex. Circuit 34 is suitably an adaptive filter.

Additionally, the system illustrated in FIG. 3 may be subject to external control, as by a programmer 62. Programmer 62 may be any suitable device, preferably a complex programmer device, although a simple hand-held magnet which is brought into close proximity to the implanted device can also be used. The implanted device contains a transmitter receiver unit 61, which is in two-way communication with the programmer 62. By this means, the implanted device can download data held in diagnostic unit 52. Also, it can pick up initiation signals, to initiate insulin pumping via control 55, or initiate stimulation of the pancreas directly.

The functions illustrated in FIG. 3 are suitably carried out under software control. Microprocessor 48 includes memory for holding an appropriate control algorithm and data. It is to be understood that blocks such as 34, 42, 44, 46, 50 and 52 may be incorporated within the microprocessor.

Figure 4:
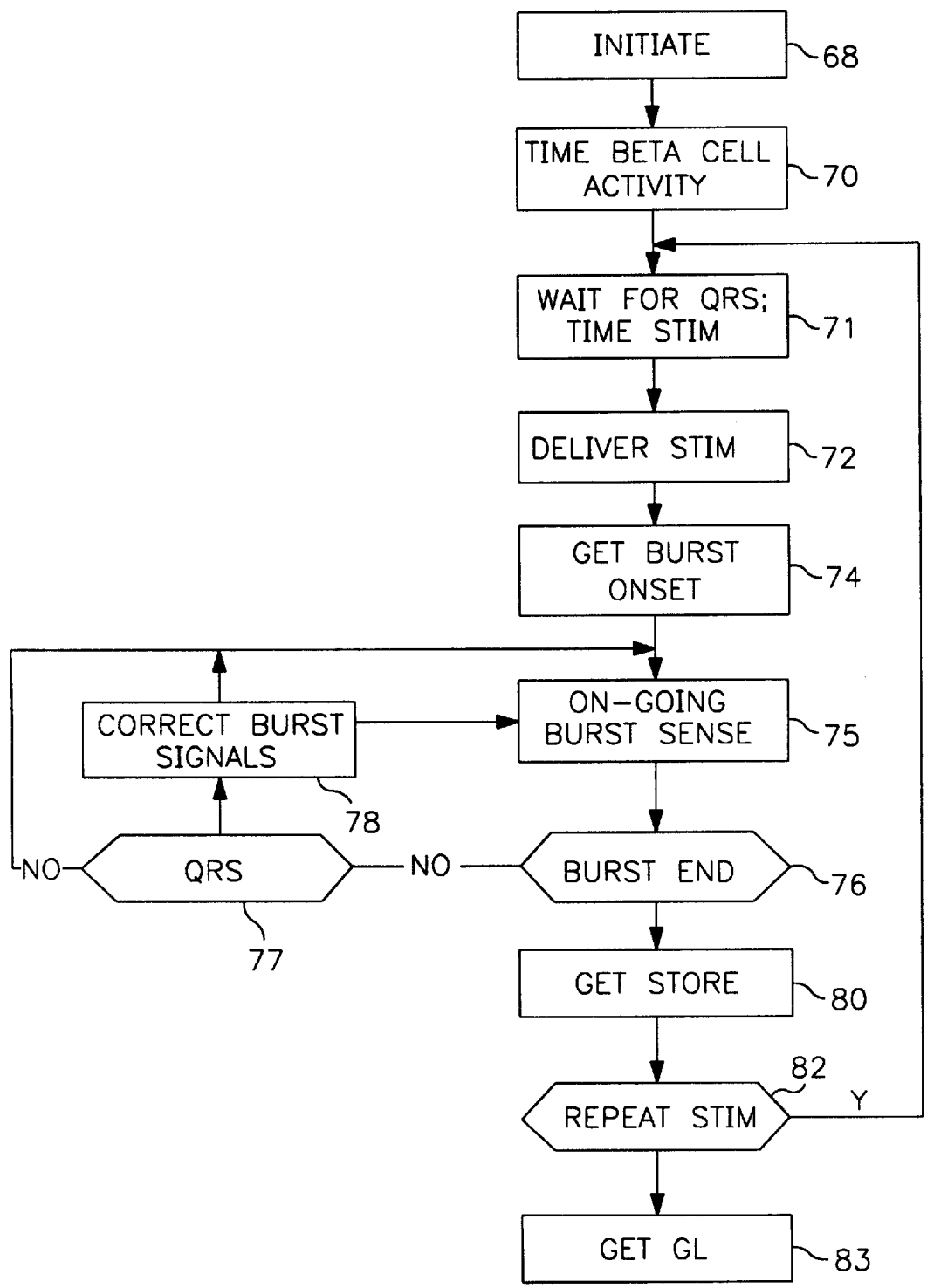
FIG. 4 is a flow diagram illustrating the primary steps taken in stimulating pancreatic beta cells and obtaining glucose level information from the insulin-producing beta cells, in accordance with this invention.

Referring to FIG. 4, there is illustrated a flow diagram of the primary steps taken in accordance with this invention, for measuring glucose level. It is to be understood that these steps are suitably carried out under software control. The software program or routine is initiated at block 68. This initiation may be done automatically, i.e., every so many minutes. Alternately, it can be initiated in response to a signal from external programmer 62. Initiation may include setting of reference parameters for evaluating glucose, e.g., the correlation between $T_B$ and blood glucose. Following initiation, at 70 the device monitors beta cell activity over a number of depolarization-repolarization cycles, to determine as best as possible the approximate onset of a next burst phase. It is a premise of this routine that some degree of beta cell activity can be sensed without enhancing stimulation. If the appropriate onset can be determined, then a stimulus can be timed for delivery before, but just shortly before, the start of the next expected spontaneous burst. This enables minimizing the influence of the stimulus on the burst duration, so that the subsequently measured duration reflects insulin demand as accurately as possible. After this, as indicated at 71 the system waits for a quiet period and for the sensing of a QRS. When a QRS is detected, the initiation of a stimulus is timed after a delay. The routine preferably waits until just before the next spontaneous burst, and delivers a stimulus if the delay following the last QRS is acceptable to avoid delivery coincident with a QRS. At 72, a stimulus is delivered to the pancreas, and at 74 the onset of the beta cell burst is obtained, i.e., the time of the start of the burst is stored in memory. As indicated at block 75, during the burst duration, the system continually senses, to measure spike frequency if available, but primarily to detect the end of the burst. As indicated at 76, if a burst end has not been found, the system continues at 77 to monitor the heart sensor output, and determine whether a QRS is occurring. If a QRS has occurred, the interference of the QRS signal is corrected out, as indicated at block 78. Although now shown in FIG. 4, other artifacts are also corrected with an adaptive filter. When the burst end has been determined, the routine gets the burst duration $T_B$, as indicated at 80. Then, at 83, it is determined whether another stimulus should be delivered. If yes, the routine loops back to block 71. Although not shown, a delay may be built in between the end of one burst and delivery of a next stimulus to produce the next synchronized burst. At 83, a measure of glucose level is obtained from the stored value or values of $T_B$, in accordance with a predetermined correlation between $T_B$ and the patient's blood glucose. This correlation is suitably determined at the time of implant, and programmed into memory; it can be adjusted by re-programming.

It is to be noted that the purpose of the stimulation is to improve the accuracy of the measurement. If no initial approximation of burst onset can be determined without stimulation, i.e., step 70 above, then stimulation can commence at a predetermined rate, switchably determined by prior testing and stored; the response is monitored by measuring the depolariztion. The stimulus rate is then increased until all stimuli yield capture, i.e., initiate a new burst; when this is achieved, the burst duration is measured. Alternately, vagal nerve stimulation can be applied to lower the spontaneous burst rate, enabling the electric field stimulation to take over at a predetermined lower rate.

Figure 5A:
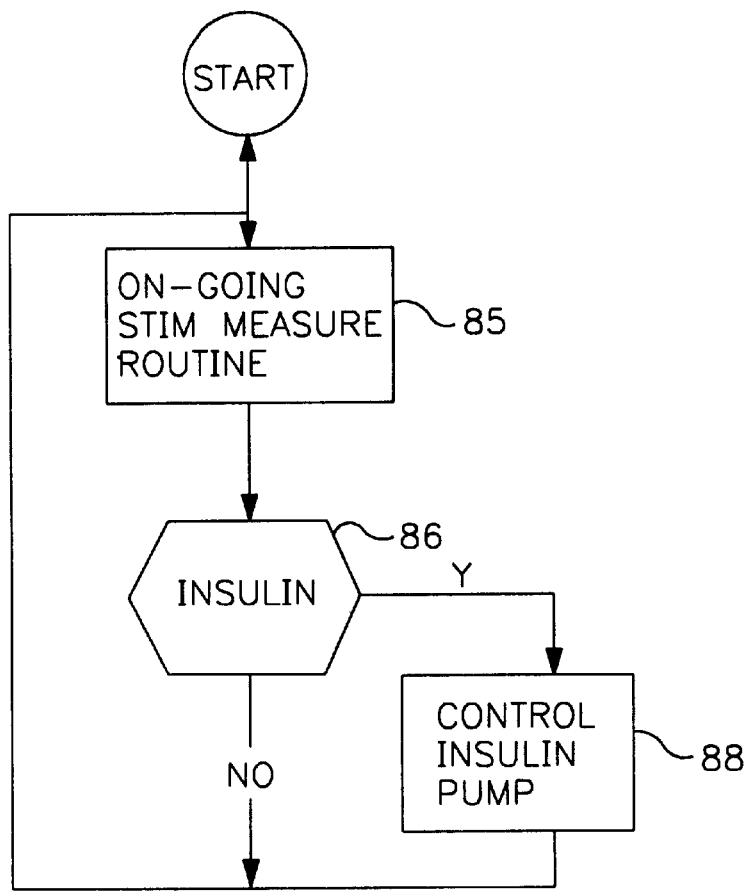
FIG. 5A is a simplified flow diagram showing the primary steps of an automatic implantable closed loop insulin-delivery system in accordance with this invention.

Referring now to FIG. 5A, there is shown a simplified flow diagram of a closed loop control for an automatic implantable system in accordance with this invention. At 85, the system carries out ongoing stimulation of the pancreas, and concurrent measurement of the beta cell activity, according to the illustrative routine of FIG. 4. At 86, the measured data is processed and a determination is made as to whether insulin is to be delivered. For example, if the blood glucose measure derived from $T_B$, and/or any other parameters of the sensed beta-cell signal, is greater than a stored value, then inulin is indicated. If yes, as indicated at 88, the insulin pump is controlled to deliver insulin to the patient. Alternately, or in addition to delivering insulin through an implanted pump, the pancreas can be stimulated so as to increase endogenous pancreatic insulin production.

Figure 5B:
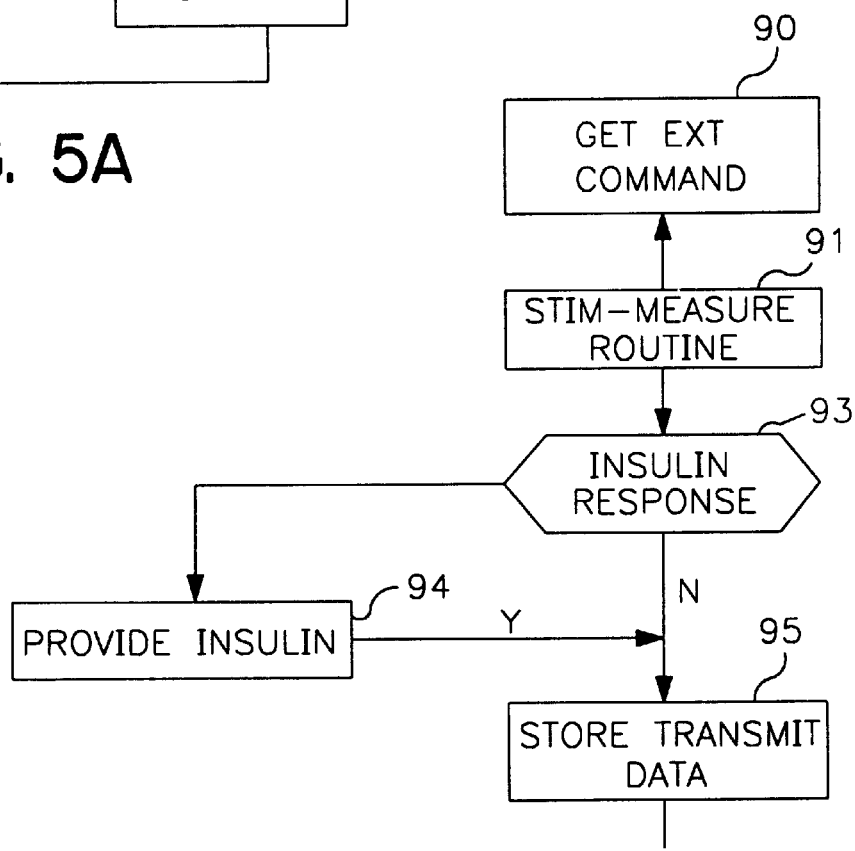
FIG. 5B is a simplified flow diagram illustrating the primary steps in a system in accordance with this invention, wherein the system responds to an external programming command.

At FIG. 5B, there is shown a simplified flow diagram of the primary steps of an alternate embodiment where the implanted device responds to an external command. The external command is received at 90, either from a programmer which communicates with telemetry or from a simpler device such as a hand held magnet. When a signal is received, the stimulate-measure routine of FIG. 4 is initiated and carried out, as illustrated at 91. After completion of this measurement routine, at 93 the device determines whether an insulin response is indicated. If yes, at 94, insulin is provided, by delivery from an implanted pump, or by stimulating the pancreas so as to induce greater insulin production. See Application Ser. No. 08/876,610, filed on the same date as this application and titled "System and Method For Enhancement of Glucose Production by Stimulation of Pancreatic Beta Cells," File No. P-7328. Then, at 95, data concerning the measured glucose level and the response is stored and/or transmitted to the external programmer, for evaluation and diagnostic purposes.

The preferred embodiments of the invention have been illustrated in terms of stimulating the pancreas. However, the invention is equally applicable to working the stimulation-sensing routine on transplanted pancreatic beta cells, e.g., transplanted islets of Langerhans, either allo, auto or xeno type. Thus, in FIG. 3 the stimulus generator can be connected to deliver stimulus pulses to, and receive depolarization-repolarization signals from a beta cell transplant (T), exclusive of the pancreas or together with the pancreas.

What is claimed is:

1. A system for sensing insulin demand of a patient, comprising:

stimulating means for delivering stimulating pulses to the pancreas of said patient;

sensing means for sensing the electrical responses of said pancreas to said stimulating pulses and obtaining signals representative of said responses;

processing means for processing said signals and deriving therefrom a measure of the insulin demand of said patient;

insulin means for delivering insulin to said patient; and delivery control means for controlling said insulin means to deliver insulin as a function of said insulin demand measure.

2. The system as described in claim 1, wherein said system is implantable, and further comprising external means for communicating to said implantable system commands for stimulating said pancreas and obtaining said insulin demand measure.

* * * * *